(12) United States Patent
Huang et al.

(10) Patent No.: US 10,076,522 B2
(45) Date of Patent: Sep. 18, 2018

(54) SYSTEMS AND METHODS FOR TREATING BACTERIAL INFECTION

(71) Applicant: Motif BioSciences Inc., New York, NY (US)

(72) Inventors: David Huang, Houston, TX (US); Keith A. Bostian, Union, NJ (US); William G. Kramer, North Potomac, MD (US)

(73) Assignee: Motif Biosciences Inc., New York, NY (US)

( * ) Notice: Subject to any disclaimer, the term of this patent is extended or adjusted under 35 U.S.C. 154(b) by 0 days.

(21) Appl. No.: 15/586,021

(22) Filed: May 3, 2017

(65) Prior Publication Data

US 2017/0319582 A1 Nov. 9, 2017

Related U.S. Application Data

(60) Provisional application No. 62/331,623, filed on May 4, 2016, provisional application No. 62/469,781, filed on Mar. 10, 2017.

(51) Int. Cl.
| | |
|---|---|
| *A61K 31/506* | (2006.01) |
| *A61K 9/00* | (2006.01) |
| *A61K 9/08* | (2006.01) |
| *A61K 31/501* | (2006.01) |

(52) U.S. Cl.
CPC .......... *A61K 31/506* (2013.01); *A61K 9/0019* (2013.01); *A61K 9/08* (2013.01); *A61K 31/501* (2013.01)

(58) Field of Classification Search
CPC .................................................. A61K 31/506
See application file for complete search history.

(56) References Cited

U.S. PATENT DOCUMENTS

| | | | |
|---|---|---|---|
| 5,773,446 A | 6/1998 | Masciardri | |
| 2009/0253722 A1* | 10/2009 | Gillessen | A61K 31/505 514/275 |

OTHER PUBLICATIONS

Morgan et al., Iclaprim: a novel dihydrofolate reductase inhibitor for skin and soft tissue infections, Future Microbiology, vol. 4, No. 2, 131-143, 2009.*
Barton et al., Future treatment options for Gram-positive infections-looking ahead, Clinical Microbiology and Infection, vol. 15, Supplement 6, Dec. 2009, pp. 17-25.*
NCT02600611, Nov. 6, 2015, available at https://clinicaltrials.gov/archive/NCT02600611/2015_11_06.*
Andrews, J. et al., "Concentrations in Plasma, Epithelial Lining Fluid, Alveolar Macrophages and Bronchial Mucosa After a Single Intravenous Dose of 1.6 mg/kg of Iclaprirn (AR-100) in Healthy Men", *Journal of Antimicrobial Chemotherapy*, Oxford University Press, vol. 60, No. 3, Sep. 1, 2017, pp. 677-680.
Anonymous, "NCT02607618 on Mar. 21, 2016: ClinicalTrials.gov Archive", Mar. 21, 2016, https://clinicaltrials.gov/archive/NCT02607618/2016_03_21, retrieved on Jun. 8, 2017, 3 pages.
McClain, Sarah L. et al., "Advances in the Medical Management of Skin and Soft Tissue Infections", *BMJ* (Clinical Research Edition), Dec. 14, 2016, vol. 355. p. i6004, 14 pages.
Krievins, D. et al., "Multicenter, Randomized Study of the Efficacy and Safety of Intravenous Iclaprim in Complicated Skin and Skin Structure Infections", *Antimicrobial Agents and Chemotherapy*, vol. 53, 0o. 7, May 4, 2009, pp. 2834-2840.
Arpida AG, "Arpida AG Iclaprim Concentrate for Solution for Infusion Advisory Committee Briefing Book", Anti-Infective Drug Advisory Committee Meeting Tentatively Scheduled for Nov. 20, 2008, Nov. 20, 2008, https://www.fda.gov/ohrms/dockets/ac/08/briefing/2008-4394b3-03-ARPIDA.pdf, retrieved on Jun. 6, 2017, pp. 1-116.
Bach, Tiffany H. et al., "Present and Emerging Therapies for Methicillin-Resistant *Staphylococcus aureus* Skin and Soft Tissue Infections: Focus on Iclaprim", *Clinical Medicine Reviews in Therapeutics*, Jun. 1, 2011, pp. 191-201.
Food and Drug Administration, "Iclaprim for the Treatment of Complicated Skin and Skin Structure Infections", FDA Briefing Document for Anti-Infective Drug Advisory Committee Meeting, Nov. 20, 2008, https://www.fda.gov/ohrms/dockets/ac/08/briefing/2008-4394b3-01-FDA.pdf, retrieved on Jun. 6, 2017, pp. 1-31.
Kohlhoff, Stephan A. et al., "Iclaprim", *Expert Opinion on Investigational Drugs*, vol. 16, No. 9, Sep. 22, 2007, pp. 1441-1448.
International Search Report and Written Opinion from Corresponding International Application No. PCT/US2017/030875, dated Jul. 11, 2017.
Hall 2nd, RG, "Fractal Geometry-Based Descrease in Trimethoprim-Sulfamethoxazole Concentrations in Overweight and Obese People", *CPT Pharmacometrics Syst. Pharmacol.*, Nov. 21, 2016, 8 pages.
Non-Final Office Action from corresponding U.S. Appl. No. 15/586,815 dated Jul. 24, 2017.
International Search Report and Written Opinion from Corresponding International Application No. PCT/US2017/031049, dated Jun. 22, 2017.

(Continued)

*Primary Examiner* — Svetlana M Ivanova
(74) *Attorney, Agent, or Firm* — DLA Piper LLP (US)

(57) ABSTRACT

Therapeutic methods, kits, dosing regimens and uses as medicament are provided, for example, for the treatment of bacterial infection. The therapeutic methods can comprise intravenously administering to a subject who has a bacterial infection a pharmaceutical composition comprising a fixed amount of iclaprim. The administration of the fixed amount can achieve a $C_{max(ss)}$ below about 800 ng/mL, a T>MIC of between about 30% to about 95% and a ratio of AUC/MIC of about 20 to about 85, and the bacterial infection can be treated. The fixed amount can be about 70 mg to about 100 mg. The pharmaceutical composition can be infused into the subject about 1 to about 3 times a day daily over a time period of about 0.75 hours to about 4 hours.

29 Claims, No Drawings

(56) References Cited

OTHER PUBLICATIONS

Van Westreenen, Mireille et al., "New Antimicrobial Strategies in Cystic Fibrosis", *Pediatr Drugs*, Dec. 2010, vol. 12, Issue 6, pp. 343-352.

* cited by examiner

SYSTEMS AND METHODS FOR TREATING BACTERIAL INFECTION

TECHNICAL FIELD

Embodiments of the present disclosure relate generally to systems and methods for treating bacterial infection and, in particular, systems and methods comprising administration of Iclaprim in a fixed dose.

BACKGROUND

Iclaprim (MTF-100, which is also known as AR-100) is a potent inhibitor of microbial dihydrofolate reductase (DHFR) that is used to treat subjects with, for example, acute bacterial skin, skin structure infections (ABSSSI) and/or hospital-acquired bacterial pneumonia (HABP). Iclaprim is a targeted Gram-positive broad-spectrum bactericidal antibiotic, which has a low propensity for resistance development. Iclaprim also exhibits an alternative mechanism of action against bacterial pathogens, including Gram-positive isolates of many staphylococcal, streptococcal, and enterococcal genera, as well as various Gram-positive pathogens that are resistant to antibiotic treatment; e.g., methicillin-resistant *Staphylococcus aureus* (MRSA). Iclaprim thus has the potential to be an effective drug for treating infections of bacteria that have become resistant to standard antibiotics.

Iclaprim has characteristics that, to date, have prevented it from being approved for clinical use in humans. For example, IV administration of iclaprim can potentially cause QTc prolongation in a dose-dependent manner. However, dosing of iclaprim at levels which do not produce a cardiac safety signal have not shown satisfactory clinical efficacy. In particular, Phase III clinical trials (ASSIST-1 and ASSIST-2 studies) evaluating the intravenous administration of a weight-based dose of iclaprim below that which caused QTc prolongation did not achieve satisfactory efficacy profiles, based on the non-inferiority margin of −10% as set by the Food and Drug Administration (FDA), including the failure to achieve an optimal ratio of AUC to minimum inhibitory concentration ("MIC") (AUC/MIC), time above the MIC (T>MIC) and steady-state maximal blood concentration ($C_{max(ss)}$). See e.g., Morgan et al., Iclaprim: a novel dihydrofolate reductase inhibitor for skin and soft tissue infections, Future Microbiology, March 2009, Vol. 4, No. 2, Pages 131-144.

Accordingly, there is a need for safe and effective therapeutic methods for intravenous administration of iclaprim for treating bacterial infection.

SUMMARY

In an embodiment, the present disclosure relates to therapeutic methods comprising intravenously administering to a subject who has a bacterial infection a pharmaceutical composition comprising a fixed amount of iclaprim. The administration of the fixed amount can achieve a $C_{max(ss)}$ below about 800 ng/mL, a T>MIC of between about 30% to about 95% and a ratio of AUC/MIC of about 20 hr to about 85 hr, and can treat the bacterial infection.

In other embodiments, the present disclosure provides kits comprising at least one dosage form comprising a pharmaceutical composition and therapeutic instructions for administering the at least one dosage form.

In other embodiments, the present disclosure provides dosing regimens comprising intravenously administering to a subject who has a bacterial infection a pharmaceutical composition comprising a fixed amount of iclaprim.

In other embodiments, the present disclosure provides uses of iclaprim to produce a medicament for the treatment of a bacterial infection, wherein the medicament is administered by a dosing regimen comprising intravenously administering to a subject who has the bacterial infection a pharmaceutical composition comprising a fixed amount of iclaprim.

DETAILED DESCRIPTION

The following detailed description is exemplary and explanatory and is intended to provide further explanation of the present disclosure described herein. Other advantages, and novel features will be readily apparent to those skilled in the art from the following detailed description of the present disclosure. Texts and references mentioned herein are incorporated in their entirety, including U.S. Provisional Patent Application Ser. No. 62/331,623 filed on May 4, 2016 and U.S. Provisional Patent Application Ser. No. 62/469,781 filed on Mar. 10, 2017.

Abbreviations

ABSSSI Acute bacterial skin and skin structure infections
ADME Absorption, Distribution, Metabolism, Excretion
AE Adverse Event
ALT Alanine Aminotransferase
ANOVA Analysis of Variance
AST Aspartate Aminotransferase
AUC Area under the Curve
b.i.d. bis in diem (twice a day)
CFU Colony Forming Units
CHO Chinese Hamster Ovary
CI Confidence Interval
CL Clearance
CrCl Creatinine Clearance
Cmax Maximum Plasma Concentration
Cmax(ss) Maximum Steady-State Plasma Concentration
Cmin Minimum Plasma Concentration
Cmin(ss) Minimum Steady-State Plasma Concentration
cSSSI Complicated Skin and Skin Structure Infections
CYP Cytochrome P 450
DHFR Dihydrofolate Reductase
ED50 Effective dose in 50% of Animals
EOT End of Treatment
F Female
HED Human Equivalent Dose
hERG Human Ether-à-go-go Related Gene
HPLC High Performance Liquid Chromatography
IC50 50% Inhibition Concentration
ITT Intent to treat
IV Intravenous
LD50 Lethal dose in 50% of Animals
M Male
MBC Minimum Bacterial Concentration
MCE Modified Clinically Evaluable
MIC50 Minimum Inhibitory Concentration for 50% of strains
MIC90 Minimum Inhibitory Concentration for 90% of strains
MITT Modified Intent-To-Treat
MRSA Methicillin-Resistant *Staphylococcus aureus*
MSSA Methicillin-Susceptible *Staphylococcus aureus*
MTD Maximum Tolerated Dose
NOAEL No Observed Adverse Effect Level p.o. Oral (per os)
PAE Post Antibiotic Effect
PAE-SME Post-antibiotic Sub-MIC Effect
Pgp P-glycoprotein
PP Per Protocol
q12h Every 12 hours
q24 h Every 24 hours
q48 h Every 48 hours
QTC Corrected QT Interval
SAE Serious Adverse Event
t½ Elimination Half-life
Tmax Time to Maximum Concentration
TK Thymidine kinase
TMP Trimethoprim
TMP-SMX Trimethoprim sulfamethoxazole
ULN Upper Limit of Normal
VISA Vancomycin Intermediate *Staphylococcus aureus*
VRSA Vancomycin Resistant *Staphylococcus aureus*
Vss Volume of Distribution at Steady State The term "subject" should be construed to include subjects, for example medical or surgical subjects, such as humans and other animals suffering from bacterial infection.

Iclaprim is a diaminopyrimidine derivative that is in the same pharmacological class as trimethoprim (TMP), and which acts as a dihydrofolate reductase-inhibiting, targeted Gram antibiotic active against Gram positive organisms. The iclaprim mesylate salt has been formulated in a sterile aqueous/ethanolic vehicle as a concentrated solution for intravenous infusion after dilution for clinical testing on humans.

Iclaprim is racemic, and nomenclature for iclaprim mesylate (International Nonproprietary Name (INN)) includes IUPAC chemical name 5-[(2RS)-2-cyclopropyl-7,8-dimethoxy-2Hchromen-5-ylmethyl] pyrimidine-2,4-diamine methanesulfonate. Other names include 5-[[(2RS)-2-cyclopropyl-7,8-dimethoxy-2H-1-benzopyran-5-yl]methyl]pyrimidine-2,4-diamine methanesulfonate. The structural formula for iclaprim mesylate is:

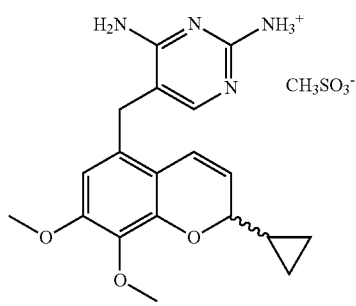

The molecular formulae for iclaprim and iclaprim mesylate are $C_{19}H_{23}N_4O_3$ (base) and $C_{20}H_{26}N_4O_6S$ (mesylate), and their relative molecular masses are 354.41 (base) or 450.52 (mesylate). General properties of iclaprim mesylate include, for example, a pH value of 4.2 for a 1% solution in water and a $pK_a$ of 7.2, a melting point range of 200-204° C., and solubility in water at 20° C. of approximately 10 mg/mL. One skilled in the art can readily obtain iclaprim or iclaprim mesylate, and synthesis of these compounds is described in U.S. Pat. No. 5,773,446, the entire disclosure of which is herein incorporated by reference.

As indicated above, pre-clinical and clinical studies indicate that iclaprim can cause QTc prolongation under certain circumstances. For example, iclaprim reversibly inhibited the hERG-mediated potassium current in transfected CHO cells, with an IC50 of 0.9 µM. In isolated rabbit Purkinje fibers, the action potential duration was increased at iclaprim concentrations above 1 µM. In contrast, the IC50 of iclaprim on the SCN5A sodium channel was found to be 95 µM and on the L-type calcium channel was found to be 46 µM, thereby suggesting that there is a selective hERG-channel inhibitory effect. Moreover, a transient QTc prolongation at $C_{max}$ was observed in human Phase I studies with iclaprim, which was pronounced at greater doses and shorter infusion times than the dose regimen foreseen for clinical use as determined by acute animal toxicity studies.

In such acute animal toxicity studies, the LD50 of IV iclaprim mesylate was determined to be >200 mg/kg in female rats and 150-200 mg/kg (HED≥20 mg/kg) in males. In the mouse, the lowest lethal IV dose was considered to be 75 mg/kg (HED 6.1 mg/kg). A repeated-dose, 4-week toxicity study was conducted in male and female rats, where single, daily IV bolus doses up to 60 mg/kg were given. In this study, histopathological changes at the injection sites were observed at dosages of 10 mg/kg/day or more, but there was no evidence of systemic toxicity. Consequently, the NOAEL was deemed to be >30 mg/kg/day (HED 3.9 mg/kg/day) of iclaprim mesylate. A 28-day toxicity study was also conducted in male and female marmosets, where iclaprim mesylate was infused intravenously over a 20-minute interval. In this study, the NOAEL was also determined to be 30 mg/kg/day (HED 3.9 mg/kg/day). In a MTD study conducted in female mini-pigs, the maximum tolerated single IV dose was determined to be 20 mg/kg (HED 14.6 mg/kg) of iclaprim mesylate.

Based on this, a single-dose ECG-study was conducted in healthy human volunteers, where 1.6 mg/kg and 3.2 mg/kg iclaprim was infused over 30 minutes. Here, iclaprim prolonged the QTc interval (QT interval corrected for heart rate) in a dose-dependent manner. Maximal increases coincided with $C_{max}$ levels and were rapidly reversible. Weight-based dosing with 1.6 mg/kg was thus assessed as acceptable for clinical purposes, whereas weight-based dosing at 3.2 mg/kg was associated with relevant QTc prolongations (>60 msec) and nonspecific T-wave alterations, and was not used for further clinical studies.

A second single-dose ECG study was conducted on healthy human volunteers using weight-based doses of 0.4 mg/kg and 0.8 mg/kg iclaprim base infused over 30 minutes and 1.6 mg/kg infused over 60 minutes. Evaluation of the QTc interval showed a reversible dose-dependent effect of iclaprim on the duration of the QTc interval at 0.8 mg/kg and 1.6 mg/kg. At both the 0.8-mg/kg and 1.6-mg/kg doses, no subject had a maximal QTc value >500 msec. When QTc was corrected according to Fridericia (QTcF), no subject exhibited any post-infusion QTcF prolongation of >60 msec from baseline. In addition, in both of the ECG studies, no gender differences concerning QTc prolongations were observed nor were any cardiovascular adverse events (AEs) reported. A transient $C_{max}$-related mean increase in QTc corrected according to Bazett (QTcB) of approximately 10 msec was observed after infusion of 0.8 mg/kg iclaprim over 30 minutes. This transient QTc prolongation is similar to or less than QTc prolongations observed with other IV-administered antibiotics; e.g., 51 msec for erythromycin, 3 to 11 msec for clarithromycin; and 9 to 17 msec for moxifloxacin. Thus, dosing with iclaprim with 0.8 mg/kg infused over 30 minutes and 1.6 mg/kg infused over 60 minutes were assessed to be safe for clinical application. Because of concerns over partitioning of iclaprim into different tissue types and the effect this had on the pharmacokinetics of the IV administered drug, the 0.8 mg/kg iclaprim weight-based dose was chosen for further clinical studies.

For example, the PK profile of 0.8 mg/kg iclaprim administered by IV was investigated in 8 subjects with mild to moderate obesity (body mass index or "BMI" 30-40) and in 8 subjects with severe obesity (BMI>40). This study showed that AUC and $C_{max}$ increased with increasing degree of obesity. The mean $C_{max}$ was 854 ng/mL in healthy subjects, 1100 ng/mL in obese subjects (BMI≥30 to <40) and 1328 ng/mL in severely obese subjects (BMI≥40). Linear regression analysis indicated a strong linear relationship between AUC (and $C_{max}$) and BMI. Thus it was clear that the body composition of the subject affected the pharmacokinetics of IV administered iclaprim, with a greater percentage of body fat causing an increase in AUC and $C_{max}$. As higher iclaprim $C_{max}$ was associated with an increased risk of toxic effects, these results indicate that caution should be taken not to overdose a subject by administering too much iclaprim with respect to the subject's BMI. Other studies showed that moderate hepatic impairment (Child-Pugh grade B) in subjects administered IV iclaprim resulted in a 2.5 fold increase in AUC and a 1.4 fold increase in $C_{max}$. Thus there is a risk of overdosing subjects with moderate hepatic impairment, which can be mitigated by reducing the IV iclaprim dose by about 50%.

One of the two initial Phase III clinical trials evaluating IV administration of 0.8 mg/kg iclaprim, given over a 0.5 hr period every 12 hr, to treat subjects suffering from cSSSIs failed to show efficacy as defined by a −10% non-inferiority margin, and the US Food and Drug Administration declined to approve this weight-based treatment for marketing in 2008. Without wishing to be bound by a particular theory, one observed disadvantage of the weight-based dosing in the previous Phase III studies is that the post-antibiotic effect achieved by the weight-based doses was not enough to sustain the T>MIC between doses. Sufficient efficacy might be achieved by increasing the amount of iclaprim administered to the subject. However, as discussed above, simply increasing the weight-based dose of iclaprim risks causing QTc prolongation.

As discussed above, iclaprim showed good anti-bacterial activity in standard rodent models of infection, and the primary PK/PD predictors for efficacy were i) the ratio of the area under the curve (AUC) to the minimum inhibitory concentration (MIC), i.e. AUC/MIC, and ii) the time above the MIC (T>MIC) expressed as a percent of the dosing interval. As discussed in more detail below, in some embodiments, the present dosing regimens produce a T>MIC of between about 30% to about 95%, for example 40% to about 70%. In some embodiments, the present dosing regimens produce further achieve a ratio of AUC/MIC of about 20 hr to about 85 hr.

A thorough QTc ("TQTc") study (see Example A below) indicated that there was an association between the maximum QTc value and the maximum plasma iclaprim concentration ($C_{max}$). Thus, minimization of $C_{max}$ should correspond to optimal cardiovascular safety of iclaprim. As shown in Example A, in some embodiment of the present dosing regimens, an iclaprim steady state $C_{max}$ in a subject of about 800 ng/mL is the reference value for risk of QTc prolongation.

The inventors have surprisingly discovered a therapeutic method for treating bacterial infection using a fixed dose of iclaprim, instead of a weight-based dose. The present dosing regimen can maximize T>MIC and minimize safety risks, for example by keeping steady state $C_{max}$ below a value that is known to result in QTc prolongation, for example below 800 ng/mL. Based on data from simulations of IV iclaprim fixed-dose regimens (64 mg, 72 mg, and 80 mg) based on the post hoc estimates of iclaprim PK in 470 subjects (discussed in more detail below in the Exemplary PopPK Model section), the inventors discovered that, for example, IV administration of about an 80 mg iclaprim fixed dose as approximately a 2-hour infusion administered q12h should provide about a 28% increase in AUC/MIC and a 32% increase in the T>MIC compared to the weight-based dosing regimen used in the previous Phase III studies discussed above, while keeping the $C_{max}$ (ss) below the reference $C_{max}$ of 800 ng/mL from the TQTc study and lower than the observed mean values for $C_{max}$ at doses >0.5 mg/kg in the TQTc studies. Therefore, the regimen of a fixed dose of iclaprim, for example about 80 mg administered q12h over a 2-hour period, can maximize the antibacterial efficacy while minimizing the potential for QTc prolongation.

As stated above, the finding that the present fixed-dose IV iclaprim regimen is efficacious while minimizing QTc prolongation in a subject is surprising, since both systemic exposure and maximum iclaprim plasma concentrations increase with increasing BMI. Using a fixed dose of iclaprim thus presents the risk of over-dosing in subjects with mild to moderate obesity and under-dosing in subjects with normal BMI. In contrast to these findings, the theoretical assumption would be that a fixed dose of iclaprim would present the risk of under-dosing in subjects with mild to moderate obesity and over-dosing in subjects with normal BMI. Those skilled in the art would therefore not be motivated to test or use a fixed dose of iclaprim to treat bacterial infections, and in fact the usual practice for IV antibiotic administration is to dose on a mg/kg basis, based on the body weight of the patient.

Embodiments of the present disclosure thus provide methods of intravascular, for example intravenous, administration to a subject who has a bacterial infection a pharmaceutical composition comprising a fixed amount of iclaprim. In one embodiment, the fixed amount is about 60 mg to about 85 mg, for example about 70 mg to about 80 mg. In one embodiment, the fixed amount is about 80 mg.

In one embodiment, administration of the fixed amount achieves a $C_{max(ss)}$ below about 800 ng/mL, for example about 500 ng/ml to about 700 ng/ml, and a T>MIC of between about 30% to about 95%, for example 40% to about 70%. In one embodiment, the administration of the fixed amount further achieves a ratio of AUC/MIC of about 20 hr to about 85 hr, for example about 25 to 80 or about 30 to about 60.

In one embodiment, intravenous administration comprises infusing the pharmaceutical composition into the subject about 1 to about 3 times a day for one or more days. In one embodiment, intravenous administration further comprises infusing the pharmaceutical composition into the subject over a time period of about 0.75 hours to about 4 hours. For example, intravenous administration can comprise infusing the pharmaceutical composition into the subject about once a day for one or more days and over a time period of about 1 to 4 hours, twice a day for one or more days and over a time period of about 0.5 to 2 hours, or three times a day for one or more days and over a time period of about 0.5 to 1 hours. In one embodiment, intravenous administration comprises infusing the pharmaceutical composition into the subject about twice a day at substantially regular intervals (q12 h) and over a time period of about 2 hours for each infusion, for one or more days.

In one embodiment, the pharmaceutical composition comprises an aqueous and/or ethanolic solution. In an embodiment, the pharmaceutical composition is reconstituted or diluted in a sterile, pharmaceutically acceptable solution prior to administration to the subject. The sterile, pharmaceutically acceptable solution can be selected, for example, from the group consisting of water, saline, lactated Ringer's solution, and Ringer's acetate solution. In one embodiment, alcohol is included for stability. When stored at 25° C., the pharmaceutical composition can be stable for a period of at least about 36 months.

In one embodiment, iclaprim is provided in a formulation as a concentrate for solution for IV use in an aqueous/ethanolic vehicle. In one embodiment, a volume of the formulated solution in ampoules (60-85 mg/5 mL) is diluted with saline to about 250-500 mL and infused q12h over a duration of about 120 minutes for each infusion, for one or more days.

In one embodiment, the fixed amount of iclaprim is administered according to the present methods to a subject that has moderate hepatic impairment. The fixed amount can be about half the amount administered to a subject that has substantially no hepatic impairment. The fixed amount can be about 30 mg to about 42.5 mg, for example about 35 mg to about 40 mg. The ordinarily skilled physician can readily determine whether a subject has moderate hepatic impairment using any suitable technique known in the art, for example by assessing the subject and assigning them a Child-Pugh score. A Child-Pugh score of "B" indicates moderate hepatic impairment.

In one embodiment, administration of the fixed amount of iclaprim to a subject according to the present methods treats a bacterial infection. As used herein, to treat a bacterial infection means that bactericidal or bacteriostatic activity is observed, and/or that one or more symptoms of the bacterial infection (e.g., redness, swelling, increased temperature of the infected area, presence of pus, fever, aches, chills, and the like) are reduced, ameliorated or delayed.

In one embodiment, the fixed amount of iclaprim is administered to a subject according to the present methods achieves substantially no occurrences of cardiotoxicity, for example substantially no occurrences of clinically significant QTc prolongation. This can be measured, for example, in a population of subjects to whom the fixed dose iclaprim is administered according to the present methods.

In one embodiment, kits comprising at least one dosage form comprising a pharmaceutical composition comprising iclaprim and instructions for administering the at least one dosage form as a fixed dose of iclaprim according to the present methods are provided. The pharmaceutical composition can comprise one or more iclaprim pharmaceutical compositions as described above. The instructions can comprise one or more of the methods of intravenous administration as described above.

In one embodiment, dosing regimens comprising intravenously administering to a subject who has a bacterial infection a pharmaceutical composition comprising a fixed amount of iclaprim according to the present methods are provided. The pharmaceutical composition can comprise one or more compositions as described above. The intravenous administration can comprise one or more of the methods as described above.

In one embodiment, uses of a medicament for treating a bacterial infection, wherein the medicament is administered by a dosing regimen are provided. The medicament can comprise one or more pharmaceutical compositions as described above. The dosing regimen can comprise one or more of the methods of intravenous administration as described above.

In therapeutic applications, compositions described herein are provided to a subject already suffering from bacterial infection or at risk from a bacterial infection, in an amount sufficient to delay or treat the bacterial infection. An amount of the present compositions comprising an active ingredient adequate to accomplish this is defined as a "therapeutically effective amount." The dosage to be used in the treatment of a specific case must be subjectively determined by, and would be apparent to, the ordinarily skilled physician or medical professional, according to the methods of the present disclosure. The variables involved for determining a therapeutically effective amount of the present compositions include the specific condition and the size, age, weight, gender, disease penetration, type of procedure, previous treatments and response pattern of the subject.

The pharmaceutical compositions can be administered intravascularly, for example intravenously. In one embodiment, the pharmaceutical compositions can be administered intravenously. The present compositions can be provided as a unit dose, for example as an infusion, which taken together comprise a therapeutically effective amount. For example, a unit dose comprising a composition of the invention can be administered once daily or multiple times daily, for example 1, 2, 3, 4, 5 or 6 times in a 12 or 24 hour period. If multiple unit doses are administered in a given time period, they can be administered at substantially even time intervals. For example, if two unit doses are administered in a 12 hour period, they can be given to the subject approximately 6 hours apart. In one embodiment, two unit doses are administered to a subject in a 24 hour period approximately 12 hours apart. Multiple unit doses are administered in a given time period can also be administered at substantially uneven time intervals. In one embodiment, a unit dosage form comprises a composition of the invention in the form of an injectable infusion for intravenous administration

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are illustrative only, since alternative methods can be utilized to obtain similar results.

Example 1

Exemplary Population PK Model

The inventors developed an exemplary Population PK ("PopPK") model for subjects with cSSSI from the Phase III "ASSIST-1" and "ASSIST-2" combined data. The PopPK analysis of the data from the ASSIST studies demonstrated no relationship between the clearance (CL) of iclaprim and body weight, leading the inventors to consider a fixed-dose rather than a weight-based dose of iclaprim, despite the risk of inducing QTc prolongation in treatment subjects. The pharmacokinetic model, based on a population PK analysis of data collected during the Phase III ASSIST clinical trials, was used to estimate the exposure to iclaprim after various fixed dosing regimens. The projected exposure profiles were assessed for their impact on PK parameters previously demonstrated to be relevant to the known safety and efficacy profile of iclaprim. Specifically, the various fixed dose regimens were examined with respect to maximizing the critical efficacy parameters, AUC/MIC and T>MIC, while minimizing $C_{max}$, the parameter previously shown to be most closely correlated with increases in QTc. Dose selections were made based upon comparison to the "base case" regimen used in ASSIST-1 and ASSIST-2, which was a weight-based iclaprim dose of 0.8 mg/kg administered as a 0.5 hr infusion, q12 h.

An iclaprim fixed dose of 80 mg/kg administered over 2 hours every 12 hours (q12 h) was selected as the dosing regimen to be progressed in pivotal Phase III clinical studies based upon exposure projections. However, the PopPK model showed that other fixed doses would also produce the desired efficacy while minimizing the safety profile.

The selected 80 mg fixed dose was designed to optimize the efficacy and safety profiles of iclaprim based on the following considerations:

When iclaprim was tested in standard rodent models of infection, good efficacy was observed. The primary PK/PD predictors for efficacy were determined to be i) the ratio of the area under the curve (AUC) to the minimum inhibitory concentration (MIC), i.e. AUC/MIC, and ii) the time above the MIC, i.e. T>MIC, expressed as a percent of the dosing interval. Thus, optimization of these two parameters was a goal of the model.

A thorough QTc (TQTc) study indicated that there was an association between the maximum QTc value and the maximum plasma iclaprim concentration ($C_{max}$). Thus, minimization of $C_{max}$ would be expected to correspond to optimal cardiovascular safety of iclaprim. In the TQTc study, doses of 1 mg/kg and 2 mg/kg administered over 0.5 hours led to dose-related increases in the QTc, whereas 0.5 mg/kg administered over 0.5 hours did not. The increases in QTc for the 1 mg/kg dose were considered to be mild, with a mean (95% confidence interval) change in the placebo- and baseline-corrected QTcB of 10.3 (3.3, 17.3) msec. This dose was associated with a geometric mean (95% confidence interval) $C_{max}$ of 792 (682, 919) ng/mL. A reference $C_{max}$ of 800 ng/mL was therefore used for the evaluation of potential dosing regimens with respect to the risk of QTc prolongation.

Iclaprim was administered at a dose of 0.8 mg/kg over 0.5 hours q12h in the ASSIST-1 and ASSIST-2 trials to 500 subjects. Iclaprim was well tolerated in both studies at this dose. Adverse events (AE) related to QTc prolongation were reported infrequently (4 cases in the iclaprim arms and 2 cases in the linezolid arms) and no cases of QTc prolongation-related cardiac effects classified as treatment related AEs were observed in these studies. Iclaprim led to a mean increase of the QTc interval by about 4 to 6 msec greater than that observed with linezolid, a drug that is not considered to cause QTC prolongation.

The ASSIST-1 and ASSIST-2 studies used sparse sampling with a population PK analysis. The post-hoc estimates of the individual subject PK parameters were used to simulate the plasma iclaprim concentration-time profiles for each subject and, from those profiles, the corresponding values for $C_{maxss}$, AUC0-24hss, AUC/MIC, and T>MIC. In these analyses, the MIC value used was based on the $MIC_{90}$ of *S. aureus* of 120 ng/mL, identified in worldwide surveillance studies. Various fixed dose regimens were examined with respect to maximizing AUC/MIC and T>MIC while minimizing the probability of a steady-state $C_{max}$ ($C_{maxss}$)≥800 ng/mL.

The calculated parameters for the proposed fixed doses of 64 mg, 72 mg, or 80 mg, administered over 1 or 2 hours every 12 hours are compared in Table 1 to the base case, 0.8 mg/kg administered over 0.5 hr every 12 hours (the dosing regimen used in the ASSIST studies). For the base case, the median AUC0-24hss was 3865 hr×ng/mL, the AUC/MIC was 32 and T>MIC was 39.17% (Table 1). While the predicted median $C_{maxss}$ for the base case regimen was 702 ng/mL, less than the reference $C_{max}$ from the TQTc study of 800 ng/mL, $C_{maxss}$ exceeded 800 ng/mL between the median (702 ng/mL) and the 75th percentile (953 ng/mL) (Table 1).

Examination of fixed doses of 64 mg, 72 mg, and 80 mg using a 1 hr infusion regimen (Table 1) indicates that while there is some improvement in AUC/MIC and T>MIC compared to the base case, the median $C_{maxss}$ is lower for 64 mg/1 hr but is increased for the 72 mg/1 hr and 80 mg/1 hr regimens, suggesting a potential increased risk of QTc prolongation at the higher doses infused over 1 hr as compared to the regimen used in the ASSIST trials.

The higher $C_{maxss}$ projected for the 1 hr infusions of 72 mg or 80 mg can be mitigated by extending the administration from 1 to 2 hr while maintaining similar overall exposure. The median AUC0-24hss for the 72 mg/2 hr and 80 mg/2 hr regimens were higher than for the base case, 4466 vs. 3875 hr×ng/mL and 4962 vs. 3875 hr×ng/mL, respectively (Table 1). These projected AUCs are somewhat higher than those achieved in Phase I clinical studies in which iclaprim was safe and well tolerated (Table 2) and represent a 1.15-fold and 1.28-fold increase, respectively, over those calculated for the base case exposure from the ASSIST-1 and ASSIST-2 trials. However, these levels are significantly below the AUCs achieved at the NOAEL in the 13-week toxicology studies (26,900 hr×ng/mL (males) and 26,600 hr×ng/mL (females) in the marmoset and 7260 hr×ng/mL (males) and 20,400 hr×ng/mL (females) in the rat.

The median $C_{maxss}$ for the 72 mg/2 hr and 80 mg/2 hr regimens is projected to be 590 ng/mL and 655 ng/mL, respectively (Table 1), lower than the 702 ng/mL predicted for the base case and lower than the observed mean values for $C_{max}$ observed at doses associated with QTc prolongation in the TQTc studies (Table 2). For both regimens, the upper limit of the 95% confidence interval for $C_{max}$ for the 1 mg/kg dose in the TQTc study, 919 ng/mL, was not exceeded until the 90th percentile (Table 1), suggesting a good safety margin.

As mentioned above, based on animal models of infection, the efficacy of iclaprim is a function of both AUC/MIC ratio and T>MIC. As a consequence of the higher AUC that can be achieved by giving a higher dose with a longer infusion time to reduce the $C_{max}$, the median AUC/MIC ratio is also projected to be higher for both the 80 mg/2 hr regimen (41 hr) and the 72 mg/2 hr regimen (37 hr), improvements of 1.28- and 1.16-fold, respectively, as compared to the base case (32 hr, Table 1). Similarly, the T>MIC is also projected to be higher for both the 72 mg/2 hr and 80 mg/2 hr regimens compared to the base case, with median T>MIC of 48.33% and 51.67% of the dosing interval, respectively (Table 1), 1.23- and 1.32-fold greater than the base case value of 39.17%. For both regimens, the median $C_{maxss}$ was lower than for the base case used in the ASSIST trials, 590 ng/mL and 655 ng/mL, respectively, for 72 mg/2 hr and 80 mg/2 hr (Table 1), representing respectively 84% and 93% of the median value of 702 ng/mL for the base case, thus optimizing the margin of safety.

Thus, the data from the simulations of the fixed dose regimens based on the post-hoc estimates of iclaprim PK in 500 subjects indicate that administration of 80 mg as a 2 hr infusion should provide a 28% increase in AUC/MIC and a 32% increase in the T>MIC compared to the dosing regimen used in the previous ASSIST trials, while keeping $C_{maxss}$ below the reference $C_{max}$ of 800 ng/mL (as determined from the TQTc study) and lower than the observed mean values for $C_{max}$ at doses >0.5 mg/kg in the TQTc studies. Therefore, the regimen of 80 mg fixed dose administered over 2 hr Q12H can maximize the likelihood of antibacterial efficacy while minimizing the potential for QTc prolongation. The other fixed dose dosing regimens modelled also showed acceptable efficacy while minimizing the potential for QTc prolongation.

Methods for the Exemplary PopPK Model

A two-compartment population pharmacokinetic model was fit to Day 4 data (at steady state) from ASSIST-1 AND ASSIST-2 subjects (N=500). The model assumes that age and sex affect clearance, that severity of infection affects intercompartmental clearance, that weight affects apparent central volume of distribution and that the apparent peripheral volume of distribution is not affected by any subject characteristic. Bayesian estimates of the individual pharmacokinetic parameters were derived. These individual parameter estimates were estimated as part of the original mod-

TABLE 1

Comparison of Exposure Metrics Among Projected Iclaprim Dosing Regimens

| Parameter | Regimen* | Percentiles | | | | | | |
|---|---|---|---|---|---|---|---|---|
| | | 5th | 10th | 25th | Median | 75th | 90th | 95th |
| $Cmax_{ss}$ (ng/mL) | 0.8 mg/kg/0.5 hr | 405 | 472 | 572 | 702 | 953 | 1,327 | 1,549 |
| | 64 mg/1 hr | 383 | 431 | 508 | 647 | 854 | 1,143 | 1,276 |
| | 72 mg/1 hr | 431 | 484 | 571 | 728 | 961 | 1,286 | 1,435 |
| | 80 mg/1 hr | 479 | 538 | 635 | 809 | 1,068 | 1,429 | 1,595 |
| | 64 mg/2 hr | 310 | 346 | 411 | 524 | 679 | 862 | 979 |
| | 72 mg/2 hr | 349 | 389 | 462 | 590 | 764 | 969 | 1,102 |
| | *80 mg/2 hr* | *388* | *433* | *514* | *655* | *849* | *1,077* | *1,224* |
| T > MIC (%)† | 0.8 mg/kg/0.5 hr | 20.00 | 22.50 | 27.50 | 39.17 | 55.00 | 71.67 | 87.50 |
| | 64 mg/1 hr | 23.33 | 25.83 | 31.67 | 40.83 | 57.50 | 76.25 | 89.17 |
| | 72 mg/1 hr | 25.83 | 27.50 | 34.17 | 45.00 | 61.67 | 82.50 | 96.67 |
| | 80 mg/1 hr | 27.50 | 30.00 | 36.67 | 48.33 | 65.83 | 87.50 | 99.17 |
| | 64 mg/2 hr | 25.83 | 29.17 | 35.00 | 45.00 | 60.83 | 80.00 | 93.33 |
| | 72 mg/2 hr | 29.17 | 31.67 | 38.33 | 48.33 | 65.00 | 86.67 | 99.17 |
| | *80 mg/2 hr* | *30.83* | *33.33* | *40.83* | *51.67* | *70.00* | *91.67* | *99.17* |
| $AUC(0-24)_{ss}$ (hr × ng/mL) | 0.8 mg/kg/0.5 hr | 1,979 | 2,192 | 2,892 | 3,865 | 5,394 | 6,903 | 8,168 |
| | 64 mg/1 hr | 2,145 | 2,463 | 3,092 | 3,970 | 5,540 | 6,978 | 7,781 |
| | 72 mg/1 hr | 2,414 | 2,771 | 3,479 | 4,466 | 6,233 | 7,850 | 8,754 |
| | 80 mg/1 hr | 2,682 | 3,079 | 3,865 | 4,962 | 6,926 | 8,722 | 9,726 |
| | 64 mg/2 hr | 2,145 | 2,463 | 3,092 | 3,970 | 5,540 | 6,978 | 7,781 |
| | 72 mg/2 hr | 2,414 | 2,771 | 3,479 | 4,466 | 6,233 | 7,850 | 8,754 |
| | *80 mg/2 hr* | *2,682* | *3,079* | *3,865* | *4,962* | *6,926* | *8,722* | *9,726* |
| AUC/MIC (hr) | 0.8 mg/kg/0.5 hr | 16 | 18 | 24 | 32 | 45 | 58 | 68 |
| | 64 mg/1 hr | 18 | 21 | 26 | 33 | 46 | 58 | 65 |
| | 72 mg/1 hr | 20 | 23 | 29 | 37 | 52 | 65 | 73 |
| | 80 mg/1 hr | 22 | 26 | 32 | 41 | 58 | 73 | 81 |
| | 64 mg/2 hr | 18 | 21 | 26 | 33 | 46 | 58 | 65 |
| | 72 mg/2 hr | 20 | 23 | 29 | 37 | 52 | 65 | 73 |
| | *80 mg/2 hr* | *22* | *26* | *32* | *41* | *58* | *73* | *81* |

*All regimens are in terms of the free base and are administered Q12H. The base case is in bold text and the chosen regimen is in italic text.
†Percent of the dosing interval with a concentration > MIC.

TABLE 2

Summary of Exposure to Iclaprim in Phase I Studies

| Study | Regimen | Dose*† | Cmax (ng/mL)‡ | AUC (hr × ng/mL)‡ |
|---|---|---|---|---|
| HMR 00-038 | Single Dose | 0.25 mg/kg (5 min) | 686 ± 279 (4) | 598 ± 270 (4) |
| | | 0.5 mg/kg (5 min) | 1,913 ± 1,265 (4) | 988 ± 168 (4) |
| | | 1 mg/kg (5 min) | 4,726 ± 1,816 (4) | 2,575 ± 757 (3) |
| | | 2 mg/kg (5 min) | 8,306 ± 1,918 (4) | 4,280 ± 406 (4) |
| HMR 01-014 | Multiple Dose Q12H × 9 days | 75 mg/10% PG§ (20 min) | 1,294 (7) | 1,665 (7) |
| | | 150 mg/10% PG§ (20 min) | 2,351 (4) | 3,603 (4) |
| | | 150 mg/EtOH & NS§ (20 | 1,869 (4) | 3,221 (4) |
| HMR 02-011 | Single Dose | 2 mg/kg (0.5 hr) | 2,085 ± 514 (5) | 4,043 ± 1,345 (5) |
| | | 4 mg/kg (0.5 hr) | 4,023 ± 772 (5) | 6,814 ± 2,711 (5) |
| AR-100-ECG-002 | Single Dose | 2 mg/kg (0.5 hr) | 1,484 [22.4] (23) | 4,423 [24.1] (23) |
| | | 4 mg/kg (0.5 hr) | 2,851 [19.2] (23) | 8,894 [29.0] (23) |
| AR-100-ECG-003 | Single Dose | 0.5 mg/kg (0.5 hr) | 373 [23.2] (24) | 996 [26.8] (24) |
| | | 1 mg/kg (0.5 hr) | 792 [34.7] (24) | 1,980 [32.7] (24) |
| | | 2 mg/kg (1 hr) | 1,102 [27.1] (24) | 3,808 [32.4] (24) |

*Doses are in terms of the maleate salt of which 80% is composed of the free base, i.e. 1 mg/kg of the salt = 0.8 mg/kg of the free base. † The duration of the injection/infusion is shown in parenthesis.
‡Arithmetic mean ± standard deviation (N) except Study HMR 01-014 for which the standard deviation was not included in the report and for Studies AR-100-ECG-002 and AR-100-ECG-003 for which the geometric mean [geometric coefficient of variation] (N) is reported.
§PG = propylene glycol; EtOH = ethanol; NS = Normal Saline elling process. The individual parameters used for the calculations were not the population-typical values, but were the Bayesian estimates of each subject's own pharmacokinetic parameters of Day 4, which represent steady-state conditions and which were used to generate the individual concentration-time profiles. Based on these individual values, the derived parameters AUC0-24 $h_{ss}$, $C_{maxss}$, $Cmin_{ss}$, AUC/MIC, and T>MIC were calculated.

A template data set was constructed in order to perform the calculations, which had the individual pharmacokinetic parameters embedded. Concentrations were generated using a NONMEM control stream. For each dosing strategy, concentrations were generated for 0.25, 0.5, 0.75, 1, 1.25, 1.5, 2, 3, 4, 5, 6, 7, 8, 9, 10, 11, and 12 hours post-start of infusion at steady-state (using Day 4 parameters). These simulation time points were employed in all simulations below. Finally, the 5th, 10th, 25th, median, 75th, 90th, and 95th percentiles of the iclaprim concentrations at each time point were calculated and are presented here.

PK-Exposure variables for steady-state conditions were estimated using the subject's own parameters and refer to a 24-hour time period. Area under the concentration-time curve ($AUC_{0-24hss}$) was calculated as AUC0-24hss=2×Dose/Clearance for q12h dosing. For calculation of the peak or maximum concentration ($C_{maxss}$), it was assumed that this occurred at the end of the infusion (0.5, 1 or 2 hours). Minimum or trough concentration (Cminss) was calculated as the concentration for time 0 before starting an infusion. The 5th, 10th, 25th, median, 75th, 90th, and 95th percentiles of these parameters were calculated and are presented here.

The PK/PD parameters AUC/MIC and T>MIC were calculated using each subject's individual PK parameters and the $MIC_{90}$ of Staphylococcus aureus (120 ng/mL). The 5th, 10th, 25th, median, 75th, 90th, and 95th percentiles of these parameters were calculated and are presented here.

The second objective of this study was met by statistically comparing the mean AUC0-24 $h_{ss}$, $Cmax_{ss}$, $Cmin_{ss}$, and T>MIC with a repeated-measures analysis of variance (ANOVA). All pharmacokinetic parameters except T>MIC were log-transformed before analysis. Since each subject's parameters were estimated for each dosage strategy, the multiple parameters produced for each subject as repeated-measures were considered. The repeated-measures ANOVA compares the different PK parameters within a subject, which is considered a more powerful test than a method that ignores the repeated-measures structure of the data. The percentage of subjects with Cmaxss values greater than 800 ng/mL was compared across dosage strategies with a repeated-measures logistic regression.

Comparison of PK and PK/PD Parameters Across Dosing Strategies

The distributions of PK and PK/PD parameters are compared descriptively in Tables 3, 5, 6, 8, 9, 11, and 13. The mean parameters were compared statistically with a repeated-measures analysis of variance (ANOVA) or a repeated-measures logistic regression, as appropriate. These comparisons are illustrated in Tables 4, 7, 10, 12 and 14. Continuous PK parameters were log-transformed before comparison.

Comparison of $AUC_{0-24ss}$ Across Dosing Strategies

The distribution of $AUC_{0-24ss}$ was the same for the same dosing strategy given IV over different time periods (i.e., comparing 64 mg given IV over 1 hour or 2 hours). The distribution of the fixed dose of 64 mg IV over 1 hour was similar to the weight-based dosing strategy. The $AUC_{0-24ss}$ distribution was smallest for the weight-based dosing strategies and largest for the fixed dose of 80 mg (Table 3). The weight-based dosage distributions were more variable than the fixed dosages. Statistically, there were no differences between the two weight-based dosing strategies; all other doses had statistically significantly larger mean AUC0-24ss (p-value<0.0001) (see Table 4). The distributions of $AUC_{0-24ss}$/MIC for the eight dosing strategies are presented in Table 5.

Comparison of $C_{maxss}$ Across Dosing Strategies

The distribution of $C_{maxss}$ was higher for dosing strategies given IV over shorter durations. The distribution of $C_{maxss}$ for the fixed dose of 64 mg IV over 1 hour was similar to the 0.8 mg/kg IV over 1 hour. The lowest $C_{maxss}$ values were observed for the 64 mg IV over 2 hours dosing; those for the 80 mg IV over 1 hour were highest (Table 6). Statistically, all dosing strategies differed from the 0.8 mg/kg IV over 0.5 hours (p-value<0.05) (see Table 7). The distributions of $C_{maxss}$/MIC for the eight dosing strategies are presented in Table 8. The percentages of subjects with $C_{maxss}$ values above 800 ng/mL are presented in Table 9. These percentages were compared statistically with a repeated-measures logistic regression; these results are presented in Table 10. All dosing strategies except the fixed dose of 72 mg differ statistically (p-value<0.05) from the 0.8 mg/kg IV over 0.5 hours.

Comparison of $Cmin_{ss}$ Across Dosing Strategies

The distribution of $Cmin_{ss}$ was the highest in the fixed 80 mg given IV over 2 hours dose and lowest for the weight-based dose 0.8 mg/kg given IV over 0.5 hours (Table 11), indicating that the fixed dose of 80 mg over 2 hours should be superior to the other regimens with respect to trough plasma levels. Statistically, all dosing strategies differed from the 0.8 mg/kg IV over 0.5 hours (p-value<0.0001) (see Table 12).

Comparison of Percentage Time Above MIC Across Dosing Strategies

The distribution of T>MIC (%) was the highest in the fixed 80 mg over 2 hours dose and lowest for the weight-based dose given IV over 0.5 hours (Table 13). Statistically, all dosing strategies differed from the 0.8 mg/kg IV over 0.5 hours (p-value<0.0001) (see Table 14). These data, surprisingly, indicate that the 80 mg fixed dose, given over 2 hr, should be superior to the previously tested dose of 0.8 mg/kg, given over 0.5 hr, with respect to parameters associated with improved efficacy.

In summary, the data from the simulations of the fixed dose regimens based on the post-hoc estimates of iclaprim PK in 470 subjects indicate that administration of 80 mg as a 2 hr infusion should provide a 28% increase in AUC/MIC and a 32% increase in the T>MIC compared to the dosing regimen used in the previous ASSIST trials, while keeping $C_{maxss}$ below the reference $C_{max}$ of 800 ng/mL as determined from the TQTc study and lower than the observed mean values for $C_{max}$ at doses >0.5 mg/kg in the TQTc studies. Therefore, the regimen of 80 mg administered over 2 hr Q12H can maximize the likelihood of antibacterial efficacy while minimizing the potential for QTc prolongation. The other fixed dose dosing regimens modelled also showed acceptable efficacy while minimizing the potential for QTc prolongation.

TABLE 3

Summary of $AUC_{0-24ss}$ percentiles across dosing strategies

| | AUC 0-24 hours Percentiles | | | | | | |
|---|---|---|---|---|---|---|---|
| Dosing Strategy | $5^{th}$ | $10^{th}$ | $25^{th}$ | Median | $75^{th}$ | $90^{th}$ | $95^{th}$ |
| 0.8 mg/kg 0.5 h iv | 1979 | 2192 | 2892 | 3865 | 5394 | 6903 | 8168 |
| 0.8 mg/kg 1 h iv | 1979 | 2192 | 2892 | 3865 | 5394 | 6903 | 8168 |
| 64 mg 1 h iv | 2145 | 2463 | 3092 | 3970 | 5540 | 6978 | 7781 |
| 72 mg 1 h iv | 2414 | 2771 | 3479 | 4466 | 6233 | 7850 | 8754 |
| 80 mg 1 h iv | 2682 | 3079 | 3865 | 4962 | 6926 | 8722 | 9726 |
| 64 mg 2 h iv | 2145 | 2463 | 3092 | 3970 | 5540 | 6978 | 7781 |
| 72 mg 2 h iv | 2414 | 2771 | 3479 | 4466 | 6233 | 7850 | 8754 |
| *80 mg 2 h iv* | *2682* | *3079* | *3865* | *4962* | *6926* | *8722* | *9726* |

*All regimens are in terms of the free base and are administered Q12H. The base case is in bold text and the chosen regimen is in italic text.
†Percent of the dosing interval with a concentration > MIC.

TABLE 4

Comparison of mean steady-state $AUC_{0-24\ hours}$ across dosing strategies.
Steady-state AUC 0-24 hours

| Comparison | Ratio of means | Standard Error | t-value | p-value | 95% CI |
|---|---|---|---|---|---|
| 0.8 mg/kg/ 1 h v 0.8 mg/kg/ 0.5 h | 100% | 0.01 | 0.00 | 1.0000 | (0.99, 1.01) |
| 64 mg/ 1 h v 0.8 mg/ kg/0.5 h | 103% | 0.01 | 5.91 | <.0001 | (1.02, 1.05) |
| 72 mg/ 1 h v 0.8 mg/ kg/0.5 h | 116% | 0.01 | 26.33 | <.0001 | (1.15, 1.18) |
| 80 mg/ 1 h v 0.8 mg/ kg/0.5 h | 129% | 0.01 | 44.59 | <.0001 | (1.28, 1.31) |
| 64 mg/ 2 h v 0.8 mg/ kg/0.5 h | 103% | 0.01 | 5.91 | <.0001 | (1.02, 1.05) |
| 72 mg/ 2 h v 0.8 mg/ kg/0.5 h | 116% | 0.01 | 26.33 | <.0001 | (1.15, 1.18) |
| *80 mg/ 2 h v 0.8 mg/ kg/0.5 h* | *129%* | *0.01* | *44.59* | *<.0001* | *(1.28, 1.31)* |

*All regimens are in terms of the free base and are administered Q12H. The base case is in bold text and the chosen regimen is in italic text.
†Percent of the dosing interval with a concentration > MIC.

TABLE 5

Summary of $AUC_{0-24ss}$/MIC percentiles across dosing strategies.

| | $AUC_{0-24ss}$/MIC Percentiles | | | | | | |
|---|---|---|---|---|---|---|---|
| Dosing Strategy | $5^{th}$ | $10^{th}$ | $25^{th}$ | Median | $75^{th}$ | $90^{th}$ | $95^{th}$ |
| 0.8 mg/kg/0.5 h | 16 | 18 | 24 | 32 | 45 | 58 | 68 |
| 0.8 mg/kg/1 h | 16 | 18 | 24 | 32 | 45 | 58 | 68 |
| 64 mg/1 h | 18 | 21 | 26 | 33 | 46 | 58 | 65 |
| 72 mg/1 h | 20 | 23 | 29 | 37 | 52 | 65 | 73 |
| 80 mg/1 h | 22 | 26 | 32 | 41 | 58 | 73 | 81 |
| 64 mg/2 h | 18 | 21 | 26 | 33 | 46 | 58 | 65 |
| 72 mg/2 h | 20 | 23 | 29 | 37 | 52 | 65 | 73 |
| *80 mg/2 h* | *22* | *26* | *32* | *41* | *58* | *73* | *81* |

*All regimens are in terms of the free base and are administered Q12H. The base case is in bold text and the chosen regimen is in italic text.
†Percent of the dosing interval with a concentration > MIC.

TABLE 6

Summary of $C_{maxss}$ percentiles across dosing strategies

| | $C_{maxss}$ (ng/mL) Percentiles | | | | | | |
|---|---|---|---|---|---|---|---|
| Dosing Strategy | $5^{th}$ | $10^{th}$ | $25^{th}$ | Median | $75^{th}$ | $90^{th}$ | $95^{th}$ |
| 0.8 mg/kg/0.5 h | 405 | 472 | 572 | 702 | 953 | 1327 | 1549 |
| 0.8 mg/kg/1 h | 355 | 415 | 505 | 623 | 836 | 1127 | 1261 |
| 64 mg/1 h | 383 | 431 | 508 | 647 | 854 | 1143 | 1276 |
| 72 mg/1 h | 431 | 484 | 571 | 728 | 961 | 1286 | 1435 |
| 80 mg/1 h | 479 | 538 | 635 | 809 | 1068 | 1429 | 1595 |
| 64 mg/2 h | 310 | 346 | 411 | 524 | 679 | 862 | 979 |
| 72 mg/2 h | 349 | 389 | 462 | 590 | 764 | 969 | 1102 |
| *80 mg/2 h* | *388* | *433* | *514* | *655* | *849* | *1077* | *1224* |

*All regimens are in terms of the free base and are administered Q12H. The base case is in bold text and the chosen regimen is in italic text.
†Percent of the dosing interval with a concentration > MIC.

TABLE 7

Comparison of mean $C_{maxss}$ (ng/mL) across dosing strategies.
$C_{maxss}$ (ng/mL)

| Comparison | Ratio of means | Standard Error | t-value | p-value | 95% CI |
|---|---|---|---|---|---|
| 0.8 mg/kg/ 1 h v 0.8 mg/kg/ 0.5 h | 87% | 0.01 | −21.70 | <.0001 | (0.86, 0.88) |
| 64 mg/ 1 h v 0.8 mg/ kg/0.5 h | 90% | 0.01 | −16.25 | <.0001 | (0.89, 0.91) |
| 72 mg/ 1 h v 0.8 mg/ kg/0.5 h | 102% | 0.01 | 2.53 | 0.0114 | (1.00, 1.03) |
| 80 mg/ 1 h v 0.8 mg/ kg/0.5 h | 113% | 0.01 | 19.33 | <.0001 | (1.12, 1.14) |
| 64 mg/ 2 h v 0.8 mg/ kg/0.5 h | 72% | 0.01 | −53.01 | <.0001 | (0.71, 0.73) |
| 72 mg/ 2 h v 0.8 mg/ kg/0.5 h | 81% | 0.01 | −34.23 | <.0001 | (0.80, 0.82) |
| *80 mg/ 2 h v 0.8 mg/ kg/0.5 h* | *90%* | *0.01* | *−17.42* | *<.0001* | *(0.89, 0.91)* |

*All regimens are in terms of the free base and are administered Q12H. The base case is in bold text and the chosen regimen is in italic text.
†Percent of the dosing interval with a concentration > MIC.

TABLE 8

Summary of $C_{maxss}$/MIC percentiles across dosing strategies.

| | $C_{maxss}$/MIC (ng/mL) Percentiles | | | | | | |
|---|---|---|---|---|---|---|---|
| Dosing Strategy | $5^{th}$ | $10^{th}$ | $25^{th}$ | Median | $75^{th}$ | $90^{th}$ | $95^{th}$ |
| 0.8 mg/kg/0.5 h | 3 | 4 | 5 | 6 | 8 | 11 | 13 |
| 0.8 mg/kg/1 h | 3 | 3 | 4 | 5 | 7 | 9 | 11 |
| 64 mg/1 h | 3 | 4 | 4 | 5 | 7 | 10 | 11 |
| 72 mg/1 h | 4 | 4 | 5 | 6 | 8 | 11 | 12 |
| 80 mg/1 h | 4 | 4 | 5 | 7 | 9 | 12 | 13 |
| 64 mg/2 h | 3 | 3 | 3 | 4 | 6 | 7 | 8 |
| 72 mg/2 h | 3 | 3 | 4 | 5 | 6 | 8 | 9 |
| *80 mg/2 h* | *3* | *4* | *4* | *5* | *7* | *9* | *10* |

*All regimens are in terms of the free base and are administered Q12H. The base case is in bold text and the chosen regimen is in italic text.
†Percent of the dosing interval with a concentration > MIC.

TABLE 9

Percentage of $C_{maxss}$ values >800 ng/mL.

| Dose | Cmaxss >800 |
|---|---|
| 0.8 mg/kg/0.5 h | 38.51% |
| 0.8 mg/kg/1 h | 28.30% |
| 64 mg/1 h | 30.21% |
| 72 mg/1 h | 41.70% |
| 80 mg/1 h | 51.91% |
| 64 mg/2 h | 14.47% |
| 72 mg/2 h | 21.49% |
| *80 mg/2 h* | *29.36%* |

*All regimens are in terms of the free base and are administered Q12H. The base case is in bold text and the chosen regimen is in italic text.
†Percent of the dosing interval with a concentration > MIC.

TABLE 10

Comparison of percentage of subjects with $C_{maxss}$ >800 ng/mL across dosing strategies.
Percentage $C_{maxss}$ >800 ng/mL

| Comparison | Odds Ratio | Standard Error | $\chi^2$ value | p-value | 95% CI |
|---|---|---|---|---|---|
| 0.8 mg/kg/ 1 h v 0.8 mg/kg/ 0.5 h | 0.63 | 0.04 | 52.52 | <.0001 | (0.56, 0.71) |
| 64 mg/1 h v 0.8 mg/kg/0.5 h | 0.69 | 0.05 | 25.16 | <.0001 | (0.60, 0.80) |
| 72 mg/1 h v 0.8 mg/kg/0.5 h | 1.14 | 0.08 | 3.48 | 0.0620 | (0.99, 1.31) |
| 80 mg/1 h v 0.8 mg/kg/0.5 h | 1.72 | 0.13 | 50.58 | <.0001 | (1.48, 2.00) |
| 64 mg/2 h v 0.8 mg/kg/0.5 h | 0.27 | 0.03 | 129.23 | <.0001 | (0.22, 0.34) |
| 72 mg/2 h v 0.8 mg/kg/0.5 h | 0.44 | 0.04 | 85.91 | <.0001 | (0.37, 0.52) |
| *80 mg/2 h v 0.8 mg/ kg/0.5 h* | *0.66* | *0.05* | *25.66* | *<.0001* | *(0.57, 0.78)* |

*All regimens are in terms of the free base and are administered Q12H. The base case is in bold text and the chosen regimen is in italic text.
†Percent of the dosing interval with a concentration > MIC.

TABLE 11

Summary of $C_{minss}$ percentiles across dosing strategies.

| | $C_{minss}$ (ng/mL) Percentiles | | | | | | |
|---|---|---|---|---|---|---|---|
| Dosing Strategy | 5th | 10th | 25th | Median | 75th | 90th | 95th |
| 0.8 mg/kg/0.5 h | 3 | 7 | 12 | 22 | 44 | 70 | 98 |
| 0.8 mg/kg/1 h | 3 | 7 | 13 | 24 | 46 | 73 | 102 |
| 64 mg/1 h | 4 | 8 | 14 | 25 | 45 | 77 | 104 |
| 72 mg/1 h | 4 | 9 | 16 | 28 | 50 | 87 | 117 |
| 80 mg/1 h | 5 | 10 | 18 | 31 | 56 | 97 | 130 |
| 64 mg/2 h | 5 | 9 | 16 | 27 | 49 | 84 | 110 |
| 72 mg/2 h | 5 | 10 | 18 | 31 | 55 | 95 | 124 |
| *80 mg/2 h* | *6* | *11* | *20* | *34* | *62* | *105* | *138* |

*All regimens are in terms of the free base and are administered Q12H. The base case is in bold text and the chosen regimen is in italic text.
†Percent of the dosing interval with a concentration > MIC.

TABLE 12

Comparison of mean $C_{minss}$ (ng/mL) across dosing strategies.
$C_{minss}$ (ng/mL)

| Comparison | Ratio of means | Standard Error | t-value | p-value | 95% CI |
|---|---|---|---|---|---|
| 0.8 mg/kg/ 1 h v 0.8 mg/kg/ 0.5 h | 106% | 0.01 | 4.20 | <.0001 | (1.03, 1.09) |
| 64 mg/ 1 h v 0.8 mg/ kg/0.5 h | 109% | 0.01 | 6.73 | <.0001 | (1.07, 1.12) |
| 72 mg/ 1 h v 0.8 mg/ kg/0.5 h | 123% | 0.01 | 15.50 | <.0001 | (1.20, 1.26) |
| 80 mg/ 1 h v 0.8 mg/ kg/0.5 h | 137% | 0.01 | 23.34 | <.0001 | (1.33, 1.40) |
| 64 mg/ 2 h v 0.8 mg/ kg/0.5 h | 123% | 0.01 | 15.47 | <.0001 | (1.20, 1.26) |
| 72 mg/ 2 h v 0.8 mg/ kg/0.5 h | 138% | 0.01 | 24.23 | <.0001 | (1.35, 1.42) |
| *80 mg/ 2 h v 0.8 mg/ kg/0.5 h* | *154%* | *0.01* | *32.07* | *<.0001* | *(1.50, 1.58)* |

*All regimens are in terms of the free base and are administered Q12H. The base case is in bold text and the chosen regimen is in italic text.
†Percent of the dosing interval with a concentration > MIC.

TABLE 13

Summary of T > MIC (%) percentiles across dosing strategies.

| | Time above MIC (%) Percentiles | | | | | | |
|---|---|---|---|---|---|---|---|
| Dosing Strategy | 5th | 10th | 25th | Median | 75th | 90th | 95th |
| 0.8 mg/kg/0.5 h | 20.00 | 22.50 | 27.50 | 39.17 | 55.00 | 71.67 | 87.50 |
| 0.8 mg/kg/1 h | 21.67 | 24.17 | 30.00 | 40.42 | 56.67 | 73.75 | 90.00 |
| 64 mg/1 h | 23.33 | 25.83 | 31.67 | 40.83 | 57.50 | 76.25 | 89.17 |
| 72 mg/1 h | 25.83 | 27.50 | 34.17 | 45.00 | 61.67 | 82.50 | 96.67 |
| 80 mg/1 h | 27.50 | 30.00 | 36.67 | 48.33 | 65.83 | 87.50 | 99.17 |
| 64 mg/2 h | 25.83 | 29.17 | 35.00 | 45.00 | 60.83 | 80.00 | 93.33 |
| 72 mg/2 h | 29.17 | 31.67 | 38.33 | 48.33 | 65.00 | 86.67 | 99.17 |
| *80 mg/2 h* | *30.83* | *33.33* | *40.83* | *51.67* | *70.00* | *91.67* | *99.17* |

*All regimens are in terms of the free base and are administered Q12H. The base case is in bold text and the chosen regimen is in italic text.
†Percent of the dosing interval with a concentration > MIC.

TABLE 14

Comparison of mean T > MIC (%) across dosing strategies.
Time above MIC (%)

| Comparison | Difference in means | Standard Error | t-value | p-value | 95% CI |
|---|---|---|---|---|---|
| 0.8 mg/kg/ 1 h v 0.8 mg/ kg/0.5 h | 1.62 | 0.24 | 6.70 | <.0001 | (1.15, 2.10) |
| 64 mg/ 1 h v 0.8 mg/ kg/0.5 h | 2.55 | 0.24 | 10.52 | <.0001 | (2.08, 3.03) |
| 72 mg/ 1 h v 0.8 mg/ kg/0.5 h | 6.25 | 0.24 | 25.78 | <.0001 | (5.78, 6.73) |
| 80 mg/ 1 h v 0.8 mg/ kg/0.5 h | 9.42 | 0.24 | 38.83 | <.0001 | (8.94, 9.89) |
| 64 mg/ 2 h v 0.8 mg/ kg/0.5 h | 6.02 | 0.24 | 24.81 | <.0001 | (5.54, 6.49) |

TABLE 14-continued

Comparison of mean T > MIC (%) across dosing strategies.
Time above MIC (%)

| Comparison | Difference in means | Standard Error | t-value | p-value | 95% CI |
|---|---|---|---|---|---|
| 72 mg/ 2 h v 0.8 mg/ kg/0.5 h | 9.78 | 0.24 | 40.35 | <.0001 | (9.31, 10.26) |
| *80 mg/ 2 h v 0.8 mg/ kg/0.5 h* | *13.03* | *0.24* | *53.75* | *<.0001* | *(12.56, 13.51)* |

*All regimens are in terms of the free base and are administered Q12H. The base case is in bold text and the chosen regimen is in italic text.
†Percent of the dosing interval with a concentration > MIC.

Example 2

—Safety and Efficacy of Intravenous Iclaprim Versus Vancomycin

Phase III Fixed-Dose Clinical Protocols

A Phase III, randomized, double-blind, multicenter study was performed to evaluate the safety and efficacy of intravenous fixed dose iclaprim versus vancomycin in the treatment of acute bacterial skin and skin structure infections suspected or confirmed to be due to Gram-positive pathogens (REVIVE-1).

Indication

The indication studied comprised acute bacterial skin and skin structure infections (ABSSSIs) suspected or confirmed to be due to Gram-positive pathogens.

Number of Investigators and Study Centers

Approximately 80 study centers in the United States, the EU, and other countries around the world were utilized.

Objectives

The primary objective of the study was to demonstrate that iclaprim is non-inferior to vancomycin in achieving a ≥20% reduction in lesion size at 48 to 72 hours (Early Time Point [ETP]) compared to baseline in all randomized subjects (intention-to-treat (ITT)). The secondary objectives of this study included demonstrating non-inferiority of iclaprim compared to vancomycin in the ITT, microbiological ITT (mITT), modified clinically evaluable (mCE), per protocol (PP), and per-protocol microbiologically evaluable (mPP) populations for the following:

1. Resolution or near resolution of ABSSSI (clinical cure, defined by a ≥90% reduction in lesion size from the size at baseline, no increase in lesion size since ETP, and no requirement for additional antibiotics [except aztreonam and metronidazole] or unplanned significant surgical procedures after ETP other than bedside wound care) at Test of Cure (TOC) visit (7 to 14 days after the end of treatment);

2. Resolution or near resolution (≥90%) of ABSSSI at End of Therapy (EOT);

3. Resolution or near resolution (≥90%) of ABSSSI at EOT and TOC among subjects with severe infection at baseline defined by meeting one or more of the following criteria:

a. fulfilled the published definition for systemic inflammatory response syndrome (SIRS) by having ≥2 of the following findings: body temperature >38° C. or <36° C., heart rate >90 bpm, respiration rate >20 breaths/minute, and WBC >12000/mm3 or <4000/mm3 or >10% bands;

b. Evaluated as having severe tenderness or severe erythema at the infection site; and c. Positive blood cultures at baseline.

4. Time to resolution of systemic and local signs and symptoms of ABSSSI.

Additional secondary objectives include:

5. Assess microbiological outcome in the mITT, mCE, and mPP populations at EOT and TOC;

6. Establish the PK profile for iclaprim using population pharmacokinetics; and

7. Establish the safety profile of iclaprim in subjects with ABSSSI.

Study Population

The study population comprised subjects ≥18 years of age of either gender with ABSSSIs suspected or confirmed to be due to Gram-positive pathogens.

Methodology/Study Design

The study is a multicenter, randomized, double-blind study of the efficacy and safety of iclaprim compared to vancomycin. Subjects received either iclaprim or vancomycin for 5 to 14 days. Subjects were evaluated daily up to ETP, then every 48 to 72 hours through the end of treatment. If the last dose of study drug fell on a day when an evaluation was not planned, an additional evaluation visit was performed on that day (i.e., all EOT evaluations were performed on the last day [+2 days] of drug dose). Subjects were also evaluated at the TOC visit (7 to 14 days post-EOT), and had a Late Follow-Up (LFU) phone call (28 to 32 days post-first dose).

After completing screening procedures, including obtaining cultures from a clinical specimen prior to antibacterial therapy, a total of 600 subjects (300 per treatment group) were randomized (1:1) to receive either: (1) iclaprim 80 mg every 12 hours or (2) weight-based vancomycin. The infusion time and duration of treatment for both groups was 2 hours and 5 days (minimum duration) to 14 days (maximum duration), respectively.

The investigators, clinical study personnel, sponsor, and the subjects remained blinded with respect to the study drug treatment allocation. The unblinded pharmacist or his/her designee was responsible for preparation of infusions. Normal saline "dummy" infusions were used to maintain the blind where vancomycin was dosed at a different interval than q12 h.

For subjects in whom Gram staining of culturable material or cultures indicated that Gram-negative coverage is required, and for subjects in whom anaerobic pathogens are suspected or confirmed as pathogens at the infected site, aztreonam and metronidazole was administered, respectively. Concomitant antibiotics aztreonam and metronidazole were used in compliance with their respective prescribing information at the discretion of the investigator during the study treatment phase.

Systemic antibiotics (other than aztreonam and metronidazole) or topical antibiotics at the site of the ABSSSI under investigation, steroids >20 mg/day prednisolone or equivalent; and Type I A and Type III-antiarrhythmic drugs were prohibited.

Clinical Assessments

The primary endpoint for clinical response (defined as the reduction in lesion size ≥20% compared to baseline) was evaluated in all randomized subjects at ETP (48 to 72 hours post-first dose). Subjects who had died or who received rescue antibacterial therapy prior to that time were included as treatment failures. In addition, clinical outcome was evaluated by the investigator at EOT and TOC (7 to 14 days post EOT). The assessments of clinical outcome was categorized as cure, failure, or indeterminate.

Microbiological Assessments

An adequate clinical specimen for microbiologic evaluation was obtained at baseline prior to randomization. Additional clinical specimens were obtained, if clinically feasible and if the subject has persistent clinical signs or symptoms, at ETP, EOT and TOC. If the subject was discontinued from the study due to treatment failure, a clinical specimen was obtained at that time. Specimens were evaluated by the local microbiology laboratory; in addition, isolates were subcultured and sent to a central microbiology laboratory for confirmation of pathogen identity and minimum inhibitory concentrations (MICs).

Two sets of blood samples for aerobic/anaerobic cultures 10 minutes apart from different sites peripherally were obtained within 24 hours prior to the first dose of study drug. Blood cultures from intravascular devices were not permitted. Any potential pathogen were subcultured and the isolates shipped to the central laboratory. Anti-streptolysin O titers were be taken within 24 hours of the start of treatment.

Microbiological response was assessed at the subject level and at the microbiological level on the basis of results of the cultures, the susceptibilities of identified organisms, and the clinical outcome of the subject. Microbiological response by subject was determined at ETP, EOT, and TOC visits and categorized as eradication, presumed eradication, persistence, presumed persistence, indeterminate, superinfection, or recurrent infection in subjects with a Gram-positive pathogen isolated at baseline.

Pharmacokinetic Assessments

Pharmacokinetic samples were obtained from subjects on 3 occasions: following the first dose of study medication; at ETP; and at EOT. After the study was complete, the database locked, and the data unblinded, subjects randomized to iclaprim had their samples assayed.

Safety and Tolerability Assessments

All subjects who received any study drug were evaluated for safety on the basis of medical history and physical examinations, reports of clinical AEs, routine electrocardiography, and clinically significant findings from routine liver function tests, serum chemistry, hematology, coagulation, and urinalysis (UA) tests. All adverse events were recorded throughout the study period, up to and including the LFU phone call. While blinded to treatment assignment, the investigator categorized the severity of each AE and the potential for relationship to study drug. Serious AEs (SAEs) include those that were life threatening, led to prolongation of the existing hospitalization, a congenital anomaly/birth defect, or caused persistent or significant disability, incapacity, or death. Treatment-emergent AEs (TEAEs) were defined as those that start or worsen in severity during or after the first dose of study drug administration through end of study.

Number of Subjects (Planned and Analyzed)

A total of 600 subjects (approximately 300 per treatment group) were randomized (1:1) for this study. Using Farrington and Manning's method for non-inferiority (NI) testing with a 1 sided alpha of 0.025, assuming a 75% early clinical response rate in each group and a 10% non-inferiority bound delta, a sample size of 295 ITT subjects per treatment group is required for 80% power. In addition, using similar methods of NI testing with a 1-sided alpha of 0.025, assuming a 90% clinical response rate at TOC in each group and a 10% NI bound delta, a sample size of 300 subjects in the ITT population per treatment group is required for 82% power. If the initial endpoint of clinical response at ETP did not achieve statistical significance, no further statistical testing was done.

Diagnosis and Main Criteria for Inclusion

The following were the main inclusion criteria: written informed consent; ≥18 years of age; a bacterial infection of the skin with a lesion size area of at least 75 cm2 with major cutaneous abscess, cellulitis/erysipelas, and/or wound infections (caused by external trauma, e.g., needle sticks, insect bites); and the presence of purulent or seropurulent drainage before or after surgical intervention of a wound or at least 3 of the following signs and symptoms: discharge, erythema (extending at least 2 cm beyond a wound edge in one direction), swelling and/or induration, heat and/or localized warmth, and/or pain and/or tenderness to palpation.

Exclusion Criteria

The following were the main exclusion criteria: ABSSSI of the following categories: severely impaired arterial blood supply such that amputation of the infected anatomical site is likely, infected diabetic foot ulcers, infected decubitus ulcers, infected human or animal bites, necrotizing fasciitis or gangrene, uncomplicated skin or skin structure infection, self-limiting infections, skin and/or skin structure infection that can be treated by surgery alone, infections associated with a prosthetic device, and suspected or confirmed osteomyelitis; known or suspected concurrent infection or conditions requiring systemic anti-microbial treatment, prophylaxis, or suppression therapy; received more than one dose of a short-acting (i.e., q12 h dosing or less) systemic antibiotic(s) active against Gram-positive pathogens within the last 7 days, unless there is documented evidence of treatment failure or demonstrated resistance of Gram-positive pathogens to the prior antibiotic therapy.

Study Medications, Dosing and Regimen

Iclaprim was administered at a dose of 80 mg in 500 mL normal saline, infused over 2 hours q12h (every 12 hours) for 5 to 14 days. For subjects with moderate hepatic impairment (Child-Pugh Class B), iclaprim was administered at a dose of 40 mg in 500 mL normal saline, infused over 2 hours q12h for 5 to 14 days.

Vancomycin was dosed as follows: 15 mg/kg body weight in 500 mL normal saline infused over 2 hours for 5 to 14 days. Dosing interval was every q12 h, q24 h, q48 h, or dosed by daily level based on creatinine clearance. Subjects randomized to vancomycin who required dosing intervals of q24 h, q48 h, or dosed by daily level due to renal impairment received dummy infusions (normal saline) at 12 hour intervals when they are not to receive vancomycin.

Vancomycin dosing was adjusted based on trough levels to maintain a trough of either 10 to 15 mg/L for subjects with an organism whose MIC is ≤1 mg/L or 15 to 20 mg/L for subjects with an organism whose MIC is >1 mg/L. Dose adjustments made due to trough monitoring needed to be performed in such a manner as to ensure that the blind was maintained. Normal saline "dummy" infusions were used to maintain the blind for subjects randomized to vancomycin who have a dosing frequency other than q12 h.

Duration of Subject Participation in Study

The total duration of participation in the study for each subject was 29 to 33 days.

Study Populations

The intent-to-treat (ITT) population comprised all randomized subjects (primary population for efficacy analyses). Subjects were analyzed in treatment group to which they were randomized. The microbiological intent-to-treat (mITT) population comprised all randomized subjects who had a Gram-positive baseline bacterial pathogen identified as the cause of ABSSSI. The modified clinically evaluable (mCE) population comprised all subjects excluded from the PP population only because they had received prohibited concomitant or preceding antibiotic therapy active against Gram-positive pathogens. The per-protocol (PP) population comprises ITT subjects who receive at least 80% of their planned doses and provide adequate data for assessment for each of the following timepoints: ETP, EOT and TOC. This excludes subjects with Gram-negative bloodstream infections who were discontinued in order to treat the Gram-negative pathogen. The PP microbiologically evaluable population (mPP) comprises mITT subjects who received at least 80% of their planned doses and provided adequate data for assessment for each of the following timepoints: ETP, EOT, and TOC. The safety population comprised all subjects who received any study drug during the trial (primary population for safety analyses). Subjects were analyzed according to the treatment they received.

Evaluation: Efficacy

The primary efficacy endpoint was the proportion of randomized subjects who achieved an early clinical response (defined as reduction in the lesion size ≥20% compared to baseline) at 48 to 72 hours (ETP) and was evaluated among all randomized subjects (ITT population). The primary efficacy analysis was the non-inferiority (NI) of iclaprim (group 1) to vancomycin (group 2) for the proportion of subjects with a ≥20% reduction in lesion size at ETP compared to baseline.

The primary NI efficacy analysis was repeated in the mITT, mCE, the PP, and the mPP populations as secondary outcomes. The secondary endpoints were:

1. Resolution or near resolution of ABSSSI (i.e., clinical cure, defined by a >90% reduction in lesion size from the size at baseline, no increase in lesion size since ETP, and no requirement for additional antibiotics, except aztreonam and metronidazole, or unplanned significant surgical procedures after ETP other than bedside wound care) at TOC for iclaprim (80 mg q12 h) compared with vancomycin (weight-based dose) for ITT, mITT, mCE, PP, and mPP populations 2. Resolution or near resolution of ABSSSI (i.e., clinical cure, defined as a resolution of signs and symptoms of ABSSSI such that no further antibiotics are required, except aztreonam and metronidazole) at TOC for icalprim (80 mg q12 h) compared with vancomyin (weigh-based dose) for ITT populations 3. Resolution or near resolution (≥90%) of ABSSSI at EOT for ITT, mITT, mCE, PP, and mPP populations 4. Resolution or near resolution (≥90%) of ABSSSI at EOT and TOC among subjects with severe infection at baseline for ITT, mITT, mCE PP, and mPP populations 5. Time to resolution of signs and symptoms of ABSSSI from start of treatment for ITT, mITT, mCE, PP, and mPP populations 6. Subject-level bacteriological response rate at EOT and TOC for mITT, mCE, and mPP populations 7. Pathogen-level bacteriological response rate at EOT and TOC for mITT, mCE, and mPP populations Evaluation: Safety Treatment emergent AEs, SAEs, hematology, clinical chemistry, UAs, vital signs, physical examinations, electrocardiograms (ECGs), and liver function tests were evaluated.

Evaluation: Pharmacokinetics

Iclaprim plasma concentrations were used to determine population PK parameters, including Cmax, AUC to infinity (AUC0-∞), clearance, and volume of distribution. Interindividual variability (IIV) were determined for PK parameters, as well as residual variability. The potential influence of clinical characteristics (age, size, sex, hepatic function, renal function, concomitant medications, etc.) on PK parameters were evaluated.

Statistical Methods

In general, statistical tests were two-sided, and at the level of significance alpha=0.05. The non-inferiority assessment were made with a one-sided test at significance level of 0.025. Confidence intervals (CIs) were calculated at a 95% confidence level.

Continuous data were summarized by treatment group using the number of subjects in the analysis population (N), mean, standard deviation (SD), median, and range, and categorical data was summarized by treatment group using N and percentage.

Primary Efficacy Analysis

The primary efficacy analysis was the NI (at significance level 0.025) of iclaprim (group 1) to vancomycin (group 2) for the proportion of ITT subjects with a ≥20% reduction in lesion size at ETP compared to baseline. The NI bound were 10%. Let P1 be the proportion for iclaprim and P2 be the proportion for vancomycin. Equivalently, if the lower bound of the two-sided 95% CI for P1-P2 was greater than −0.100 based on the Z test with unpooled variance estimate, NI was concluded.

Secondary Efficacy Analyses

The primary NI efficacy analysis were repeated in the mITT, mCE, the PP, and the mPP populations. The secondary endpoints were resolution or near resolution of ABSSSI (ie, clinical cure) at TOC for iclaprim (80 mg q12 h) compared with vancomycin (weight-based dose), resolution or near resolution (≥90%) of ABSSSI at EOT, resolution or near resolution (≥90%) of ABSSSI at EOT and TOC among subjects with severe infection at baseline, time to resolution of signs and symptoms of ABSSSI, by-subject bacteriological response rate at EOT and TOC, and by-pathogen bacteriological response rate at EOT and TOC.

Safety Analyses

All subjects who received any amount of iclaprim or vancomycin during the trial were evaluated for safety. Safety evaluation included incidence of TEAEs, laboratory test results (including liver function tests), vital signs, ECG results, and physical examination findings. All summaries of safety data was based on the safety population (all treated subjects).

Summary tables were provided for all AEs by treatment group. The incidence of AEs, related AEs, SAEs, and AEs leading to discontinuation of the study treatment can be presented by Medical Dictionary for Regulatory Activities system organ class (SOC) and preferred term. In addition, the incidence of AEs by severity was presented by SOC and preferred term.

The AE summary tables included subject (patient) counts. Therefore, if a subject experienced more than one episode of a particular AE, the subject was counted only once for that event. If a subject had more than one AE that was coded to the same preferred term, the subject was counted only once for that preferred term. Similarly, if a subject had more than one AE within a SOC, the subject was counted only once in that SOC.

Laboratory test variables were summarized by treatment group and visit using descriptive statistics (number of subjects, mean, SD, minimum, maximum, as well as mean change from baseline, SD for mean and standard error for mean change, minimum, median, maximum, and number and percent of subjects within specified categories). Shift tables (ie, cross-tabulations of below the lower limit of the normal range, within the limits of the normal range and above the upper limit of the normal range at baseline versus scheduled visits) were presented by laboratory test. Laboratory tests with categorical results that could not be analyzed by change from baseline or shift table analysis were not included in these summaries, but are listed. Data obtained from laboratory tests not required by the protocol was not summarized, but may be listed.

Results

Data from the second Phase 3 ABSSSI Trial, REVIVE-2, expected in the second half of 2017

As detailed above, the present study comprised a 600-patient double-blinded, active-controlled, global, multi-center trial, in patients with ABSSSI that compared the safety and efficacy of an 80 mg intravenous dose of iclaprim with a 15 mg/kg intravenous dose of vancomycin. Treatments were administered every 12 hours for 5 to 14 days.

Iclaprim was well tolerated in the study, with most adverse events categorized as mild.

TABLE 15

Adverse Events Iclaprim and Vancomycin

|  | Iclaprim N = 293 | Vancomycin N = 297 |
| --- | --- | --- |
| TEAEs (Treatment Emergent Adverse Events) | 151 (51.5%) | 128 (43.1%) |
| Study drug related TEAEs | 57 (19.5%) | 53 (17.8%) |
| TEAEs leading to discontinuation of study drug | 8 (2.7%) | 13 (4.4%) |
| TEAE-related SAEs (Serious AEs) | 8 (2.7%) | 12 (4.0%) |
| Deaths | 0 (0.0%) | 1 (0.3%) |

Iclaprim achieved the primary endpoint of non-inferiority (NI) (10% margin) compared to vancomycin at the early time point (ETP), 48 to 72 hours after the start of administration of the study drug, in the intent-to-treat (ITT) patient population. Iclaprim also achieved NI (10% margin) at the test of cure (TOC) endpoint, defined as resolution of signs and symptoms of ABSSSI such that no further antibiotics were required, 7 to 14 days after study drug discontinuation, in the ITT patient population.

TABLE 16

Endpoints Iclaprim and Vancomycin

| Time Point | Endpoint | Iclaprim N = 298 | Vancomycin N = 300 | % Difference (95% CI) |
| --- | --- | --- | --- | --- |
| ETP | Early Clinical Response (ECR) | 241 (80.9%) | 243 (81.0%) | −0.13 (−6.42, 6.17) |
| TOC | Clinical cure | 251 (84.2%) | 261 (87.0%) | −2.77 (−8.39, 2.85) |

CONCLUSIONS/DISCUSSIONS

Iclaprim, given at a fixed dose of 80 mg over 2 hr, q12 hr, IV, was non-inferior to the comparator drug vancomycin in the Phase III REVIVE clinical trial in patients with ABSSSI. This is in contrast to previous data from the Phase III ASSIST-2 study, in which a weight-based dose of 0.8 mg/kg over 0.5 hr, q12 hr, given IV, did not meet the FDA criteria of non-inferiority to linezolid. The invention of the optimal dosing regimen for iclaprim was reduced to practice in the REVIVE trial, and was based on a detailed optimization of the relevant parameters of exposure as predicted from pharmacokinetic analysis, especially directed towards maximizing both AUC/MIC and T>MIC with respect to efficacy, while minimizing $C_{max}$ with respect to safety parameters.

The invention claimed is:

1. A therapeutic method consisting of:
    intravenously administering to a subject who has a bacterial infection a pharmaceutical composition consisting of a fixed amount of iclaprim,
    wherein administration of the fixed amount achieves a $C_{max(ss)}$ below 800 ng/mL, a T>MIC of between 30% to 95% and a ratio of AUC/MIC of 20 to 80,
    wherein the fixed amount is 80 mg,
    wherein the intravenous administration consists of infusing the pharmaceutical composition into the subject over a time period of 2 hours,
    and wherein the bacterial infection is treated.

2. The therapeutic method of claim 1, wherein the $C_{max(ss)}$ is 500 ng/ml to 700 ng/ml and the T>MIC is between 40% to 70%.

3. The therapeutic method of claim 1, wherein the administration of the fixed amount further achieves a ratio of AUC/MIC of 30 to 60.

4. The therapeutic method of claim 1, wherein the intravenous administration comprises infusing the pharmaceutical composition into the subject about 1 to about 3 times a day.

5. The therapeutic method of claim 1, wherein the pharmaceutical composition comprises an aqueous and/or ethanolic solution.

6. The therapeutic method of claim 5, wherein the pharmaceutical composition is reconstituted or diluted in a sterile, pharmaceutically acceptable solution prior to administration to the subject.

7. The therapeutic method of claim 6, wherein the sterile, pharmaceutically acceptable solution is selected from the group consisting of water, saline, lactated ringer's solution, and ringer's acetate solution.

8. The therapeutic method of claim 1, wherein administration of the fixed amount to a population of subjects achieves substantially no occurrences of clinically significant QTc prolongation.

9. The therapeutic method of claim 1, wherein administration of the fixed amount to a population of subjects achieves substantially no occurrences of hepatotoxicity.

10. The therapeutic method of claim 1, wherein the subject has mild to moderate hepatic impairment.

11. The therapeutic method of claim 1, wherein the bacterial infection is due to Gram-positive pathogens.

12. The therapeutic method of claim 1, wherein the bacterial infection comprises acute bacterial skin and skin structure infection.

13. A dosing regimen consisting of:
    intravenously administering to a subject who has a bacterial infection a pharmaceutical composition consisting of a fixed amount of iclaprim,
    wherein administration of the fixed amount achieves a $C_{max(ss)}$ below 800 ng/mL, a T>MIC of between 30% to 95% and a ratio of AUC/MIC of 20 to 80,
    wherein the fixed amount is 80 mg,
    wherein the fixed amount is infused into the subject 2 to 3 times a day with each infusion taking place over a time period of 2 hours,
    and wherein the bacterial infection is treated.

14. The dosing regimen of claim 13, wherein the administration of the fixed amount further achieves a ratio of AUC/MIC of 30 to 60.

15. The dosing regimen of claim 13, wherein the bacterial infection is due to Gram-positive pathogens.

16. The dosing regimen of claim 13, wherein the bacterial infection comprises acute bacterial skin and skin structure infections, or hospital acquired bacterial pneumonia.

17. A therapeutic method consisting of:
intravenously administering to a subject who has a bacterial infection a pharmaceutical composition consisting of a fixed amount of iclaprim,
wherein administration of the fixed amount achieves a $C_{max(ss)}$ below 800 ng/mL, a T>MIC of 30% to 95% and a ratio of AUC/MIC of 20 to 80,
wherein the fixed amount is 80 mg and wherein the fixed amount is infused into the subject 2 to 3 times a day with each infusion taking place over a time period of 2 hours,
and wherein the bacterial infection is treated.

18. The therapeutic method of claim 17, wherein the pharmaceutical composition comprises an aqueous and/or ethanolic solution.

19. The therapeutic method of claim 17, wherein the pharmaceutical composition is reconstituted or diluted in a sterile, pharmaceutically acceptable solution prior to administration to the subject.

20. The therapeutic method of claim 17, wherein the sterile, pharmaceutically acceptable solution is selected from the group consisting of water, saline, lactated ringer's solution, and ringer's acetate solution.

21. The therapeutic method of claim 17, wherein administration of the fixed amount to a population of subjects achieves substantially no occurrences of clinically significant QTc prolongation.

22. The therapeutic method of claim 17, wherein administration of the fixed amount to a population of subjects achieves substantially no occurrences of hepatotoxicity.

23. The therapeutic method of claim 17, wherein the subject has mild to moderate hepatic impairment.

24. The therapeutic method of claim 17, wherein the bacterial infection is due to Gram-positive pathogens.

25. The therapeutic method of claim 17, wherein the bacterial infection comprises acute bacterial skin and skin structure infection, or hospital acquired bacterial pneumonia.

26. The therapeutic method of claim 17, wherein the intravenous administration comprises infusing the pharmaceutical composition into the subject about 1 to about 3 times a day, for a period of 5 to 14 days.

27. The therapeutic method of claim 26, wherein the intravenous administration comprises infusing the pharmaceutical composition into the subject 2 times a day, for a period of 5 to 14 days.

28. The therapeutic method of claim 5, wherein the intravenous administration comprises infusing the pharmaceutical composition into the subject about 1 to about 3 times a day, for a period of 5 to 14 days.

29. The dosing regimen of claim 18, wherein the subject is administered an infusion 2 to 3 times a day for a period of 5 to 14 days.

* * * * *